United States Patent [19]

Hardtmann

[11] 4,025,511
[45] May 24, 1977

[54] N-ALKYLCARBONYLOXYALKYL ISATOIC AND 3-AZAISATOIE ANHYDRIDES

[75] Inventor: Goetz E. Hardtmann, Florham Park, N.J.

[73] Assignee: Sandoz, Inc., E. Hanover, N.J.

[22] Filed: Dec. 24, 1974

[21] Appl. No.: 536,099

[52] U.S. Cl. .................. 260/244 A; 260/251 A
[51] Int. Cl.² ............ C07D 265/00; C07D 273/00; C07D 295/00
[58] Field of Search ............. 260/244 A, 295

[56] References Cited

UNITED STATES PATENTS 3,725,321 4/1973 Wirth et al. ................ 260/244
3,729,473 4/1973 Böshagew et al. ........... 260/244

FOREIGN PATENTS OR APPLICATIONS 2,025,248 12/1970 Germany
2,144,566 3/1972 Germany
42-10835 9/1963 Japan

OTHER PUBLICATIONS

J. of Biol. Chem. 244 (11) pp. 3009–3018, (1969), Jovin et al., –"Chem. Modification of DNA Polymerase".

Primary Examiner—Albert T. Meyers
Assistant Examiner—D. W. Robinson
Attorney, Agent, or Firm—Gerald D. Sharkin; Richard E. Vila

[57] ABSTRACT

The compounds of this invention are N-alkylcarbonyloxyalkyl substituted isatoic and 3-azaisatoic anhydrides useful as intermediate for pharmacologically active compounds which are prepared by reaction of such an ahydride with a cyclic pseudothiourea.

11 Claims, No Drawings

N-ALKYLCARBONYLOXYALKYL ISATOIC AND 3-AZAISATOIE ANHYDRIDES

The compounds of the invention are intermediates useful in the preparation of compounds which may be represented by the structural formula I:

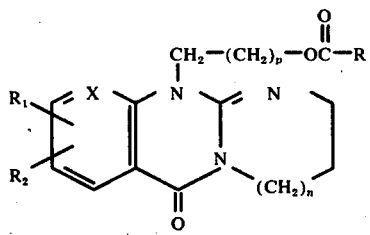

wherein
R is alkyl of 1 to 4 carbon atoms,
$p$ is 1 to 3,
X is =CH— or =N—,
each of $R_1$ and $R_2$ is hydrogen, halo of atomic weight of from 19 to 80, i.e., fluoro, chloro or bromo, alkyl of 1 to 4 carbon atoms or alkoxy of 1 to 4 carbon atoms when X is =CH— and $R_1$ is hydrogen and $R_2$ is hydrogen or alkyl of 1 to 4 carbon atoms when X is =N—, and
$n$ is 0 or 1,
or a pharmaceutically acceptable acid addition salt thereof.

The compounds of the formula I may be prepared by reaction (Step A) of a compound of the formula II:

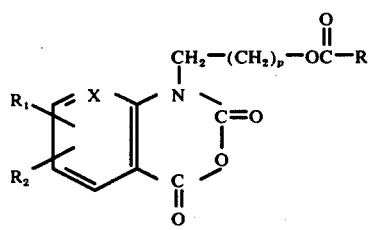

wherein R, $R_1$, $R_2$, X and $p$ are as defined, with a compound of formula III:

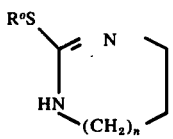

wherein $n$ is as defined and $R^o$ is lower alkyl or benzyl.

The preparation of compounds I by the reaction of Step A can be carried out at temperatures in the range of 20° C. to 160° C., more usually 20° C. to 140° C., preferably 80° C. to 120° C. The reaction is conveniently carried out in an organic solvent of conventional type providing an inert reaction medium. Cyclic ethers and aromatic solvents suitable for use at reflux temperatures represent the preferred solvents, particularly dioxane and toluene. The reaction is preferably carried out in the presence of a base, e.g., sodium hydroxide or sodium carbonate; and if the compound III is employed directly in acid addition salt form then it is desirable to employ an amount of base somewhat greater than the amount necessary to neutralize the acid. In general, the reaction product of formula I may be recovered from the reaction of Step A by working up by conventional procedures.

The compounds of the formula II are novel and valuable intermediates and may be prepared by reacting a compound of the formula IV:

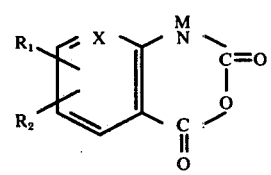

in which $R_1$, $R_2$ and X are as defined and M is hydrogen or an alkali metal, with a compound of the formula V:

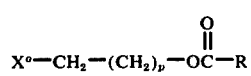

in which R and $p$ are as defined and $X^o$ is halo, e.g., chloro or bromo.

The preparation of compounds II from compounds IV and V may be carried out at temperatures of from 0° C. to 100° C. preferably 20° C. to 50° C. The reaction is conveniently effected in an inert organic solvent which may be of conventional type, e.g., dimethylacetamide. The reaction is preferably effected with a compound IV in which M is an alkali metal and such compounds are prepared in a conventional manner by reacting a compound in which M is hydrogen with a strong base such as an alkali metal hydride, e.g., sodium hydride. If the compound IV in which M is hydrogen is employed, the reaction is carried out in the presence of a strong base, e.g., an alkali metal alkoxide or hydroxide The compounds of formulae III, IV and V are either known or may be prepared from known materials by established procedures. With respect to the compounds of the formula IV (M being hydrogen) reference may be made to U.S. Pat. No. 3,622,573 and Beckwith et al., J. Chem. Soc. (C), 1968, 2756.

Also within the scope of the compounds of formula I of the invention are pharmaceutically acceptable salts not materially depreciating the pharmacological effect of the compounds. Such salts include the acid addition salts of known type, e.g., the hydrochloride, maleate and the like. The acid addition salts may be produced from the corresponding free bases by conventional procedures. Conversely, the free bases may be obtained from the salts by procedures known in the art.

The compounds of formula I are useful because they possess pharmacological activity in animals. In particular, the compounds I are useful as hypolipidemic agents, more particularly as hyperlipoproteinemic agents, as indicated by the fall of triglyceride levels in the male albino Wistar rats weighing 110–130 g. initially. The rats are maintained on drug-free laboratory chow diets for 7 days and then divided into groups of eight to 10 animals. Each group with the exception of the control is then given typically 20–100 milligrams per kilogram of body weight per diem of the compound orally for 6 days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, E., and Lederer, H., 1965, Technicon Symposium Mediad Inc., New York, (345-347) are added, and the mixture is shaken for 1 hour. Triglyceride levels is determined on the sample by Technicon N-78 (triglyceride) methodology. The change in serum triglyceride levels induced by the drug is computed as a percentage of the control triglyceride levels.

For use by hypolipidemic agents, the compounds I may be administered orally as such or admixed with conventional pharmaceutical carriers. The dosage administered may vary depending on the particular compound employed, the therapy desired and the severity of the condition being treated. In general, satisfactory results are obtained when administered orally at a daily dosage of from about 3 milligrams to about 200 milligrams per kilogram of animal body weight, preferably given in divided doses, two to four times a day, or in sustained release form. For most mammals the total oral daily dosage is from about 200 grams to about 3000 grams of the compound, and the dosage forms suitable for internal use comprise from about 50 milligrams to about 1500 milligrams of active compound in intimate admixture with a solid or liquid pharmaceutically acceptable carrier or diluent.

The compounds I are also useful as anti-inflammatory agents as indicated by an inhibition of Carrageenan induced edema in rats and a reduction in foot volume and an improvement in grip strength in the adjuvant arthritis test in rats using Mycobacteria butyricum in Freund's adjuvant, both on oral administration (15-150 mg./kg.). For use as anti-inflammatory agents, the compounds may be combined with a pharmaceutically acceptable carrier, and such other conventional adjuvants as may be necessary, and administered orally or parenterally in a conventional manner. The dosage administered will, of course, vary depending upon the compound used, the severity of the condition being treated, and the mode of administration. However, in general, satisfactory results are obtained when administered at a daily dosage of about 3 milligrams to about 200 milligrams per kilogram of body weight, preferably given in divided doses two to four times a day, or in sustained release form. For most mammals the administration of from about 200 milligrams to about 2000 milligrams of the compound per day provides satisfactory results and dosage forms suitable for internal administration comprise from about 50 milligrams to about 1000 milligrams of the compound in admixture with a solid or liquid pharmaceutical carrier or diluent.

For above usages, the compounds I may be administered orally, in such forms as tablets, dispersible powders, granules, capsules, syrups, and elixirs; and parenterally as solutions, suspensions, dispersions, emulsions, and the like, e.g., a sterile injectable solution such as an aqueous suspension. These pharmaceutical preparations may contain 0.5% up to about 90% of the active ingredient in combination with the carrier or adjuvant, more usually between 3% and 50% by weight. Such compositions may be prepared according to any method known in the art for the manufacture of pharmaceutical compositions, and such compositions may also contain one or more conventional adjuvants, such as sweetening agents, flavoring agents, coloring agents and preserving agents, in order to provide an elegant and palatable preparation.

Tablets and capsules containing the ingredients indicated below may be prepared by conventional techniques and are useful in treating lipidemia, particularly triglyceridemia, and inflammation in mammals at a dose of one tablet or capsule four times a day.

| Ingredients | Weight (mg.) Tablet | Capsule |
|---|---|---|
| 10-(2'-acetoxyethyl)-2,3-dihydro-imidazo 2,1-b quinazolin-2(1H)-one | 100 | 100 |
| Tragacanth | 10 | — |
| Lactose | 197.5 | 250 |
| Corn starch | 25 | |
| Talcum | 15 | |
| Magnesium stearate | 2.5 | |

The generally preferred compounds of the formula I are those in which X is =C—.

The following examples illustrate representative compounds of the invention and the manner in which they may be prepared.

EXAMPLE 1

10-(2'-acetoxyethyl)-2,3-dihydro-imidazo[2,1-b]quinazolin-2(10H)-one

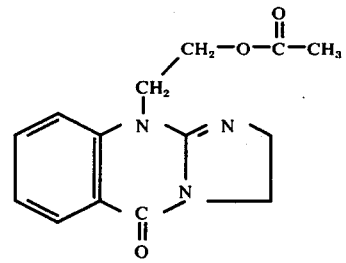

STEP A

Preparation of N-(2-acetoxyethyl)isatoic anhydride

To a solution of 30 g. of isatoic anhydride in 300 ml. of dimethylacetamide is added 9.0 g. of pentane washed sodium hydride. After stirring for 1 hour at room temperature, 33 g. of 2-bromoethylacetate is added and the mixture stirred for 17 hours at 40° C. The resulting mixture is evaporated to one third its volume, cooled and poured over 500 ml. of ice water. After one-half hour, the resulting precipitate is recovered by filtering, washed twice with water, dried under reduced pressure, dissolved in 500 ml. of methylene chloride, dried over sodium sulfate, filtered through silica gel and treated with alumina and charcoal. The methylene chloride is exchanged for diethyl ether and the resulting precipitate is recovered by filtering, washed twice with dimethyl ether and dried under reduced pressure to obtain N-(2-acetoxyethyl)isatoic anhydride, m.p. 128°-131° C.

STEP B:

Preparation of 10-(2'-acetoxyethyl)-2,3-dihydroimidazo[2,1-b]quinazolin-5(10H)-one.

A mixture of 18 g. of N-(2-acetoxyethyl)isatoic anhydride, 8.5 g. of 2-methylmercapto-imidazoline and 2 pellets of potassium hydroxide in 300 ml. of dioxane is heated at reflux for 5 hours, the solvent then evaporated off and water added. The resulting precipitate is recovered by filtering and washed twice with water. The precipitate is dissolved in methylene chloride and extracted three times with 1N. hydrochloric solution. The combined hydrochloric acid solutions and filtered through celite, sodium carbonate solution is added and the resulting precipitate is recovered by filtering, washed with water, air dried, dissolved in methylene chloride, dried, filtered and the methylene chloride exchanged for diethyl ether. The resulting precipitate is recovered by filtering, washed with cold diethyl ether and dried under reduced pressure at 40° C. to obtain 10-(2'-acetoxyethyl)-2,3-dihydro-imidazo[2,1-b]quinazolin-5(10H)-one, m.p. 124°–126° C.

EXAMPLE 1A

Following the procedure of Example 1, there is prepared 11-(2'-acetoxyethyl)-2,3,4,11-tetrahydropyrimido [2,1-b]quinazolin-6-one (free base and hydrochloride acid addition salt forms).

EXAMPLE 2

Following the procedure of Step A of Example 1, the following intermediates are prepared:

A) N-(3-acetoxypropyl)isatoic anhydride.
B) 6-chloro-N-(2-acetoxyethyl)isatoic anhydride.
C) N-(2-t-butylcarbonyloxyethyl)isatoic anhydride.
D) 6,7-dimethoxy-N-(2-acetoxyethyl)isatoic anhydride.
E) 6,7-dimethyl-N-(2-acetoxyethyl)isatoic anhydride.
F) N-(2-acetoxyethyl)-3-azaisatoic anhydride.
G) N-(4-acetoxybutyl)-3-azaisatoic anhydride.

and are used following the procedure of Step B of Example 1 to prepare respectively the following:

A-1) 10-(3'-acetoxypropyl)-2,3-dihydro-imidazo[2,1-b]quinazolin-5(10H)-one.
A-2) 11-(3'-acetoxypropyl)-2,3,4,11-tetrahydropyrimido [2,1-b]quinazolin-6-one.
B-1) 7-chloro-10-(2'-acetoxyethyl)-2,3-dihydroimidazo[2,1-b]quinazolin-5(10H)-one (free base and hydrochloride acid addition salt forms).
C-1) 10-(2'-t-butylcarbonyloxyethyl)-2,3-dihydroimidazo[2,1-b]quinazolin-5(10H)-one.
D-1) 7,8-dimethyl-10-(2'-acetoxyethyl)-2,3-dihydroimidazo[2,1-b]quinazolin-5(10H)-one.
E-1) 7,8-dimethyl-10-(2'-acetoxyethyl)-2,3-dihydro-imidazo[2,1-b]quinazolin-5(10H)-one.
F-1) 10-(2'-acetoxyethyl)-2,3-dihydro-imidazo [2,1-a]pyrido[2,3-d]-pyrimidine-5(10H)-one.
F-2) 11-(2'-acetoxyethyl)-1,2,3,4-tetrahydro-2H-pyrido[2,3-d]pyrimido[1,2-a]pyrimidin-6-one.
G-1) 10-(4'-acetoxybutyl)-2,3-dihydro-imidazo[2,1-a]pyrido[2,3-d]pyrimidin-5(10H)-one.

The compounds of the formula II are referred to herein as substituted 3-azaisatoic anhydrides and may also be referred to as 4-substituted-3,4-dihydro-1,3-dioxo-1H-pyrido [2,3-d][1,3]oxazines. For example, the compound of Example 2F may be named 4-(2-acetoxyethyl)-3,4-dihydro-1,3-dioxo-1H-pyrido[2,3-d][1,3]oxazine.

What is claimed is:

1. A compound of the formula:

wherein
R is alkyl of 1 to 4 carbon atoms,
$p$ is 1 to 3,
X is =CH— or =N—, and when X is =CH— each of $R_1$ and $R_2$ is hydrogen, fluoro, chloro, bromo, alkyl of 1 to 4 carbon atoms or alkoxy of 1 to 4 carbon atoms; and when X is =N— $R_1$ is hydrogen and $R_2$ is hydrogen or alkyl of 1 to 4 carbon atoms.

2. A compound of claim 1 in which X is =CH—.

3. A compound of claim 2 in which each of $R_1$ and $R_2$ is hydrogen.

4. The compound of claim 2 which is N-(2-acetoxyethyl)isatoic anhydride.

5. The compound of claim 2 which is N-(3-acetoxypropyl)isatoic anhydride.

6. The compound of claim 2 which is 6-chloro-N-(2-acetoxyethyl)isatoic anhydride.

7. The compound of claim 2 which is N-(2-t-butylcarbonyloxyethyl)isatoic anhydride.

8. The compound of claim 2 which is 6,7-dimethoxy-N-(2-acetoxyethyl)isatoic anhydride.

9. A compound of claim 1 in which X is =N-.

10. A compound of claim 9 in which $R_1$ and $R_2$ are each hydrogen.

11. The compound of claim 10 which is 4-(2-acetoxyethyl)-3,4-dihydro-1,3-dioxo-1H-pyrido[2,3-d][1,3]oxazine.

* * * * *